(12) United States Patent
Mead et al.

(10) Patent No.: US 6,819,421 B1
(45) Date of Patent: Nov. 16, 2004

(54) DETECTION OF NEW SPECIES OF PARTICLES

(75) Inventors: Donald C. Mead, Carlsbad, CA (US); Clay Davis, Redondo Beach, CA (US)

(73) Assignee: Point Source Technologies, LLC, Solana Beach, CA (US)

( * ) Notice: Subject to any disclaimer, the term of this patent is extended or adjusted under 35 U.S.C. 154(b) by 20 days.

(21) Appl. No.: 10/412,130

(22) Filed: Apr. 11, 2003

(51) Int. Cl.[7] .............................................. G01N 21/00
(52) U.S. Cl. ....................................................... 356/338
(58) Field of Search ............................... 356/335–343; 250/574

(56) References Cited

U.S. PATENT DOCUMENTS

| | | | |
|---|---|---|---|
| 3,770,351 A | 11/1973 | Wyatt | |
| 3,901,602 A | 8/1975 | Gravatt, et al. | |
| 4,070,113 A | 1/1978 | Frazer et al. | |
| 4,173,415 A | 11/1979 | Wyatt | |
| 4,265,538 A | 5/1981 | Wertheimer | |
| 4,541,719 A * | 9/1985 | Wyatt | 356/343 |
| 4,548,500 A * | 10/1985 | Wyatt et al. | 356/336 |
| 4,565,448 A | 1/1986 | Abbott et al. | |
| 4,679,939 A * | 7/1987 | Curry et al. | 356/336 |
| 4,702,598 A | 10/1987 | Böhmer | |
| 4,728,190 A | 3/1988 | Knollenberg | |
| 4,906,094 A | 3/1990 | Ashida | |
| 4,907,884 A | 3/1990 | Wyatt et al. | |
| 4,942,305 A | 7/1990 | Sommer | |
| 4,952,055 A | 8/1990 | Wyatt | |
| 4,987,539 A | 1/1991 | Moore et al. | |
| 5,125,737 A | 6/1992 | Rodriguez et al. | |
| 5,247,340 A | 9/1993 | Ogino | |
| 5,305,071 A | 4/1994 | Wyatt | |
| 5,414,508 A | 5/1995 | Takahashi et al. | |
| 5,436,465 A | 7/1995 | Borden et al. | |
| 5,534,999 A | 7/1996 | Koshizuka et al. | |
| 5,627,040 A | 5/1997 | Bierre et al. | |
| 5,737,078 A | 4/1998 | Takarada et al. | |
| 5,999,256 A | 12/1999 | Jones et al. | |
| 6,023,324 A | 2/2000 | Myers | |
| 6,100,541 A | 8/2000 | Nagle et al. | |
| 6,118,531 A | 9/2000 | Hertel et al. | |
| 6,120,734 A | 9/2000 | Lackie | |
| 6,313,908 B1 | 11/2001 | McGill et al. | |
| 6,421,121 B1 | 7/2002 | Haavig et al. | |
| 6,639,672 B2 * | 10/2003 | Haavig et al. | 356/338 |

FOREIGN PATENT DOCUMENTS

GB        2317228 A        3/1998

OTHER PUBLICATIONS

"Recent Overview Article—Aerosol Characterization Research at the University of Hertfordshire", by Prof. Paul Kaye, STRC Particle Instruments Research Group, Science and Technology Research Centre, University of Hertfordshire, Hatfield, United Kingdom, reproduced from the Aerosol Society Newsletter, No. 33, Sep. 18–20 1998.

"Discrimination of phytoplankton via light–scattering properties", by Philip J. Wyatt and Christian Jackson, Limnology and Oceanography, 34(1), 1989, pp. 96–112, American Society of Limnology and Oceanography, Inc.

* cited by examiner

Primary Examiner—Michael P. Stafira
(74) Attorney, Agent, or Firm—Leon D. Rosen

(57) ABSTRACT

An improvement in a system that identifies unknown microscopic particles in a fluid such as water, by detecting scattering of a laser beam (24) in multiple directions as a particle passes through a detect zone (30) to generate an event vector, and by comparing the eventvector to those of particles of known species. When the eventvectors produce a cluster (70) of particles in a multi-dimensional projection of the eventvectors, the computer signals that a possible new species has been found in the fluid. A background signature is generated for particles in the fluid when the fluid is safe. When new water is later passed through the apparatus, clusters of particles are searched for that are present in a much greater density than exists for the background signature for a safe fluid, to generate a signal indicating that the fluid may be unsafe.

9 Claims, 2 Drawing Sheets

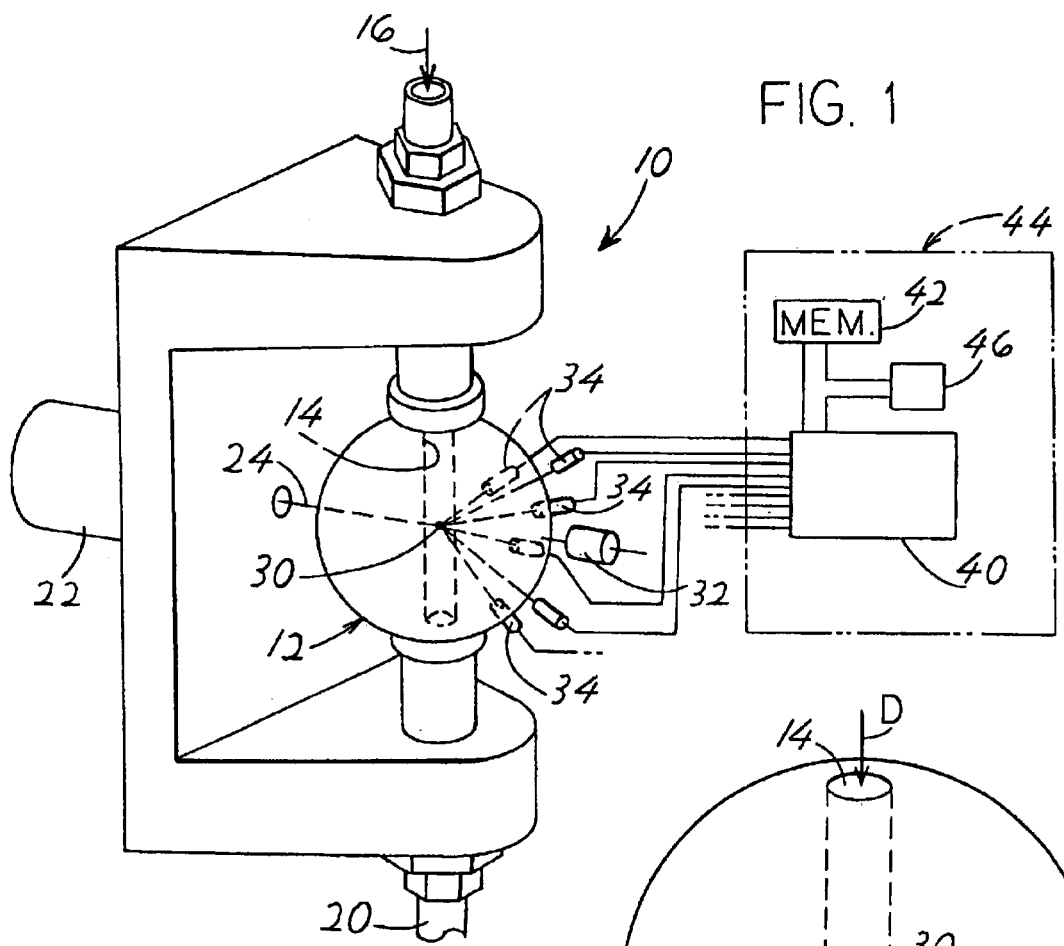
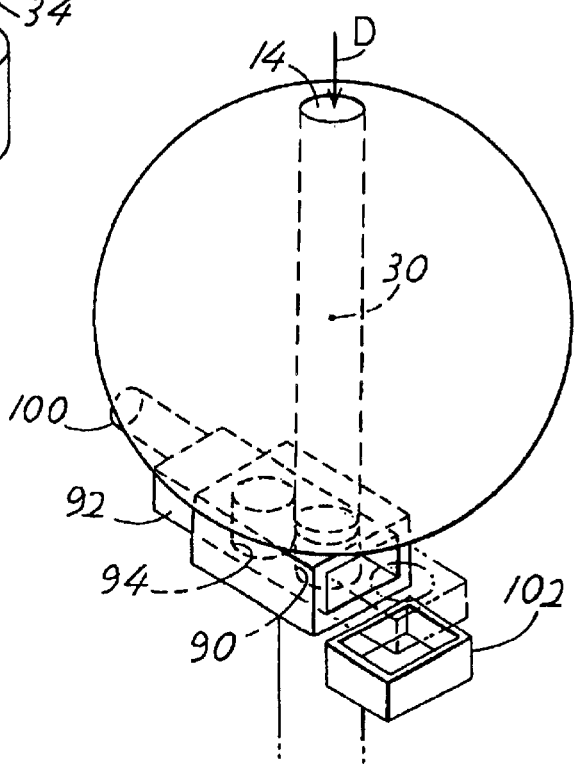
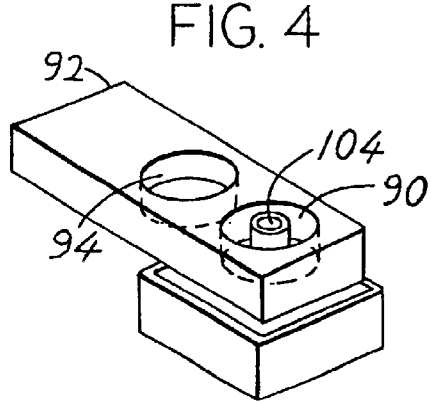

DETECTION OF NEW SPECIES OF PARTICLES

BACKGROUND OF THE INVENTION

Applicant's earlier U.S. Pat. No. 6,519,033 describes a system for identifying particles in a fluid, such as microorganisms in water. The technique includes directing a narrow laser or other light beam through the fluid. The technique also includes detecting light scattered from a particular location, called a detect zone lying along the laser beam, to each of multiple detectors, when a particle passes through the detect zone. The passage of a particle through the detect zone: is an event, and the outputs of the multiple detectors upon the occurrence of an event, is called an eventvector. Applicant first programs a computer by obtaining eventvectors for each of a plurality of different species of microorganisms of interest. For each species, this is accomplished by passing particles all of a particular known species through the device and detecting the eventvectors for particles of that known species. The multiple eventvectors for each species are contained in a memory and are analyzed by an algorithm that views the particles in multi-dimensional space, in a direction that results in the closest grouping of eventvectors of the same species and greatest separation of groups of eventvectors of different species. Many of the known species will be pathogenic organisms that will be encountered in significant numbers only in an unusual situation, as when a water treatment plant is not operating properly. The system will generate an alarm signal if a significant number of particles of a known pathogenic species is detected.

When monitoring a fluid such as water in a water treatment plant, there will be particles that do not fall into any one of the known-species whose eventvectors have been entered into the computer memory. Such particles may be particles of minerals, waste, etc. However, it is possible for a significant number of particles of a new pathogenic microorganism to be accidentally or deliberately introduced into the water supply, where multiple eventvectors of the new species have not previously been entered into the computer. It is highly desirable that the particle identification system automatically generate a signal to warn personnel of the possibility that a new species of microorganism has been introduced in significant numbers in the water supply.

A system that monitors fluids such as water, for the presence of possibly harmful microorganisms or other microscopic particles, which was sensitiva to the introduction of significant numbers of particles of a new species, would be of value.

SUMMARY OF THE INVENTION

In accordance with one embodiment of the present invention, a method and apparatus are provided for identifying clusters of a new species of microorganism in a fluid, by the analysis of light scatter patterns created by particles passing through a detect zone. The outputs of a plurality of photodetectors, when a particle passes through the detect zone and scatters light towards the photodetectors, is an eventvector. After a large number of eventvectors have been detected for a quantity of water, a computer determines the locations in a multi-dimensional projection of the eventvectors, of any clusters of eventvectors that lie outside the known-particle volumes. Upon the detection of a cluster, the computer generates an alert signal that can alert responsible personnel that a new cluster has been found.

In order to increase the accuracy of the system and decrease false alarms, a background signature of the water supply in a recent safe condition, is entered into the computer. The background signature contains multiple eventvectors for recent safe water that is similar to water now being monitored. The safety can be determined by persons drinking the water and not becoming sick over a period of a day or two. The computer then compares the eventvectors generated when a new sample of water is being monitored, to the background signature earlier provided for recently interrogated similar water that has been deemed to be safe. A considerable variance in the eventvectors for the new sample compared to the previous safe sample of water, and particularly the presence of a cluster not present in the background signature of the safe water, causes the computer to generate a signal indicating that a new species of particles has been detected. A cluster can be identified by a higher density of eventvectors in the multi-dimensional space in which the eventvectors are located in the computer.

The novel features of the invention are set forth with particularity in the appended claims. The invention will be best understood from the following description when read in conjunction with the accompanying drawings.

BRIEF DESCRIPTION OF THE DRAWINGS

FIG. 1 is a partial isometric view and partial schematic diagram, of particle identifying apparatus of the present invention.

FIG. 3 is a simplified isometric view of a modified apparatus, which is modified from the apparatus of FIG. 1.

FIG. 4 is an isometric view of a portion of the apparatus of FIG. 3.

DESCRIPTION OF THE PREFERRED EMBODIMENTS

Figure 2:
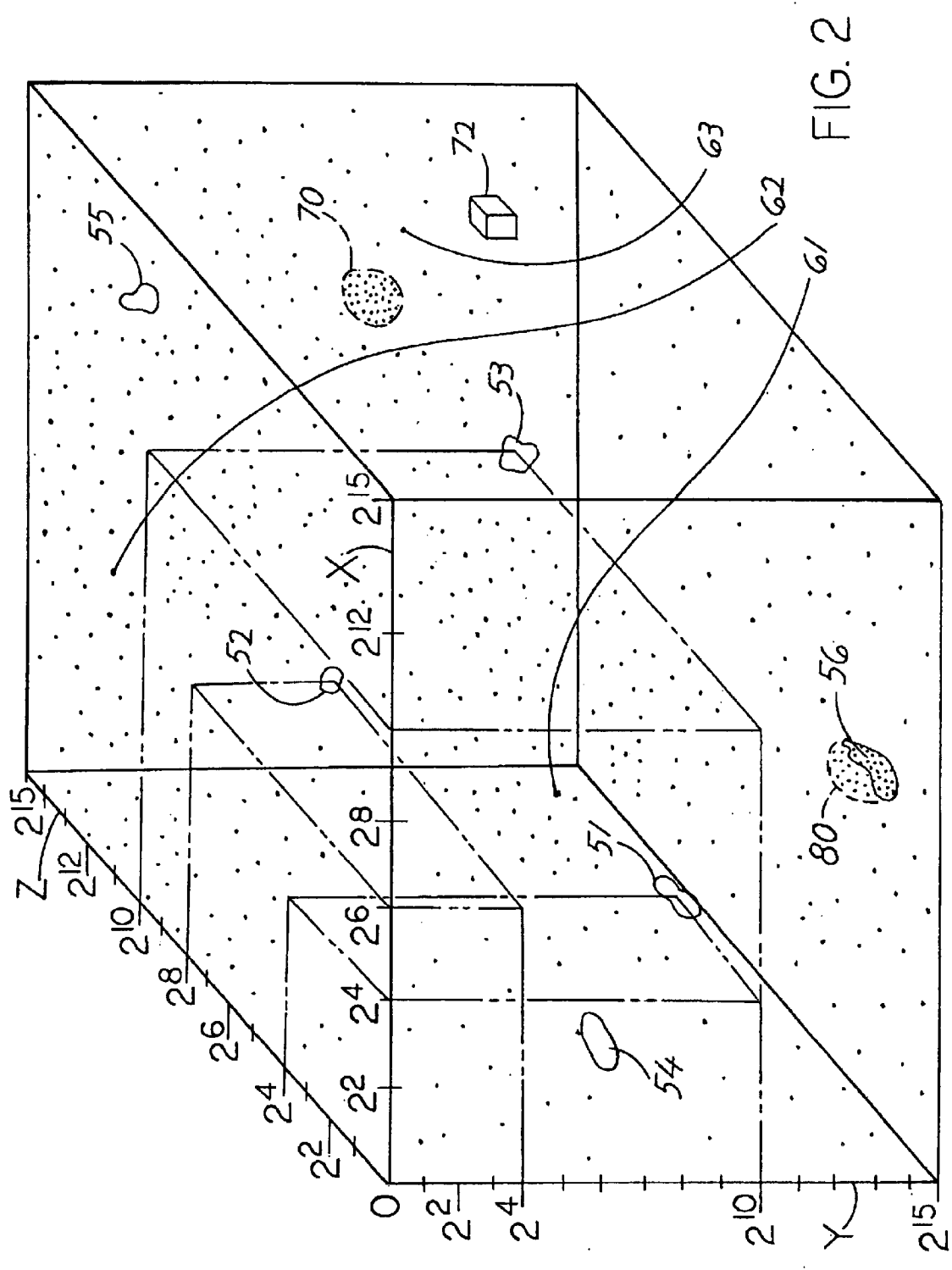
FIG. 2 is simplified three-dimensional representation of multi-dimensional analysis carried out by the apparatus of the present invention.

FIG. 1 illustrates a system 10 for identifying particles in a fluid. The system includes a carrier 12, with the particular carrier shown being largely in the form of a sphere of transparent material with a cylindrical passage 14 extending through it. The sample of water or other fluid to be monitored is directed along arrow 16, to flow through the passage 14 and out through an exit 20. A laser 22 directs a laser beam 24 in a forward direction through a detect zone 30 that lies along the vertical passage 14. Most of the laser beam 24 passes completely through the carrier to a dump 32 where the laser energy is absorbed. However, some of the laser beam is scattered by a particle passing through the detect zone 30. A plurality of photodetectors 34 detect light scattered from the detect zone 30 to the locations of the detectors. The outputs of the detectors are delivered to a processing circuit 40 of a computer 44, and are delivered to a memory 42. The computer circuit 40 includes circuitry that converts the analog outputs of, the photodetectors to digital signals, and includes a central processing unit and a program that is useful to detect the species of some particles that may be encountered and to indicate the likely presence of a new species of particles. A comparer 46 serves as a pattern recognition means that can determine if the detector outputs for a particle place that particle in one of the known species, and can make other comparisons.

FIG. 2 is a simplified example of the arrangement of data representing microscopic particles detected by the apparatus of FIG. 1. Each of the particles that is detected is microscopic, in that it can be seen only in a microscope, but is not much smaller than the wavelength of the laser beam (e.g. 0.7 nanometer). Particles of a range of about one half micron to one hundred microns can be detected. As a result of each event, when a particle passes through the detect zone, a group of numbers are generated, each representing the output of one of the multiple defectors. In the system described in U.S. Pat. No. 6,519,033, the apparatus includes sixteen detectors, which would result in sixteen numbers. In FIG. 2, applicant has plotted the numbers in three dimensions along three axes X, Y and Z, which would represent the outputs of three photodetectors, for simplification. Also, the output of each detector is represented as a power of two. This allows the output of each detector to range from 1 ($2^0$) to 65,000 ($2^{16}$).

The term "volume" is used herein to define a space in a multi-dimensional projection, where the volume generally has as many dimensions as the projection. FIG. 2 shows only three dimensions. Volumes 51–56 in FIG. 2 represent six different known-species of particles. Each volume generally contains almost all eventvectors generated for that species. This is accomplished by placing only particles, e.g. microorganisms of one species, in a sample of water, and passing that water through the apparatus 10 of FIG. 1, while recording the eventvectors. It is noted that a MONOVA (multiple analysis of variances) system has been used to analyze the data of FIG. 2, to place the eventvectors of each known-particle volume 51–56 so the eventvectors of each known-particle species are clustered as close together as possible, but the different volumes are spaced apart as far as possible (with compromises). Applicant attempts to obtain as many known-particle volumes, each representing a particular species of particle, as possible. In this way, when new particles are detected, that lie outside the known-particle volumes, attention can be concentrated on the new particles. It is noted that in FIG. 2, no particles lie in the known-particle volumes 51–56, which is usually the situation when the volumes 51–56 represent eventvectors of pathogenic species.

In any sample of water, there will be numerous particles whose eventvectors 61, 62, 63, etc. fall outside the known-particle volumes 51–56. However, if there is a sudden surge in numbers of particles that all appear to be of the same species, then it is important to take note of this, so the water sample can be analyzed by other means to determine the species of the new particle whose concentration is substantial. Applicant does this automatically by using a program that detects clusters of eventvectors, such as cluster 70 of eventvectors. Programs are available for detecting clusters of points, such as the program "MATLAB" sold by The Mathworks, Inc. of Natick, Mass. The program is used so that if there is a high density of particles (high density of eventvectors) in a small volume of multi-dimensional space, then the program generates an alert signal to indicate this.

One way of detecting a cluster is to divide the volume into small volumes such as 72 that are each of the same order of magnitude as the average known-particle volumes 51–56. The average density of particles outside the known-particle volumes 51–56 is determined. Also, the program searches for any density that is significantly above the average density in a volume 72 that is of the same order of magnitude as the average volume of the known-particle volumes 51–56. A density at least 50% greater than average, and preferably a density that is at least twice, and more preferably three times average, within the small volume 72 comparable to the volumes of the other known-particle volumes, can be considered to be a cluster. When such cluster is detected, an alert signal is generated to alert personnel that a cluster has been detected which is outside the known-particle volumes. Other techniques can be used to detect clusters, as by detecting the density of particles in tiny volumes one-twentieth the average volume of the known-particle volumes, and looking for at least four tiny volumes that lie adjacent to one another and that have a 100% greater density than the average.

When a technician receives an alert signal indicating that a cluster: has been detected, the technician takes a sample of the water that is being monitored and tests it. One type of test is a microscopic examination of the water to search for microorganisms of interest. Another technique is to grow particles that may be microorganisms, in a nutrient solution that microorganisms generally grow on, and to detect a great increase in the number of microorganisms. Perhaps after one or two days of such testing, a technician can determine the species of the cluster that has been detected.

In some situations a cluster may be detected, that lies very close to an existing known article volume. In FIG. 2, a cluster 80 is illustrated, which is close the known-particle volume 56. If the volume 56 is for a relatively harmless particle such as a species of algae, many particles may be present in volume 56. When the cluster 80 is found, it is examined as by growing in a nutrient and examining under a microscope. If it is determined that the species is the same as the species of particles in volume 56, the volume 56 may be expanded.

FIGS. 3 and 4 illustrate an apparatus that can be used to aid a technician in determining the species of a particle that has been detected in a cluster. FIG. 3 shows the detect zone 30 through which particles pass, whose light scattering patterns are detected by the eventvectors generated by photodetectors (34 in: FIG. 1). In one example, the detect zone has a horizontal width and length of 1.5 mm each and a vertical thickness of 0.15 mm. The water is assumed to be moving downwardly in the direction D, and the flow is laminar. A short period of time after a new particle has been detected that is located in the cluster shown at 70 in FIG. 2, that particle would reach a sample chamber 90. The sample chamber 90 is part of a shuttle 92 that includes a substitute chamber 94. When the particle reaches the sample chamber 90, a solenoid 100 rapidly shifts the sample chamber so its contents are dumped into a container 102. In one example, the distance between the detect zone 30 and the middle of the sample chamber 90 is 16 cm, and fluid is moving down through the passage 14 at a velocity of 8 cm per second. In that case, precisely two seconds after detection of a particle at the detect zone 30 that belongs to the cluster 70 of FIG. 2, the solenoid 100 is operated to move the fluid into the container 102. Liquid in the container 102 can be examined, with some assurance that the particle that was detected, now lies in the container 102.

As shown in FIG. 4, the sample chamber 90 can include a small center part 104 that will contain the particle, because the flow is laminar through the passage. The contents of the center part 104 can be contained in a small section of the container 102, so only a limited volume has to be examined. It is noted that when the sample chamber is moved out of line with the carrier passage 14 (FIG. 3), the substitute chamber 94 moves into its place, to continue a flow through the passage.

If a cluster is identified (e.g. by microscopic examination) as a new species, then the volume of the cluster 70 of FIG. 2 can be considered to be an additional known-particle species, and can be added to the memory of 42 of FIG. 1, so that an additional known-particle species can be readily identified in future samples of water that are interrogated. The eventvectors that make up the additional known-particle species can be transmitted to a central station, which transmits them to other monitoring systems.

Water supplies commonly contain large numbers of particles that do not fit into one of the known-particle volumes 51–56 of FIG. 2. Such particles may be minerals, animal waste particles, etc. which do not fit into a cluster, despite the cluster lying in a multi-dimensional volume that may have perhaps sixteen dimensions (corresponding to perhaps sixteen photodetectors). Although many of such particles, which lie outside the known-particle volumes, may be present, they typically will be present even if a new cluster is found, as when algae suddenly bloom and there is a large number of algae of a particular species. Preferable, the eventvectors of certain algae species are known article volumes.

To better differentiate between particles that have been continually present for a substantial period of time and a new cluster of particles that suddenly appears in a water supply, applicant supplies data to the memory 42 representing the background of particles that were recently present when the water was safe to drink. Applicant can do this by first taking a sample of water and passing it through the apparatus 10 of FIG. 1, to generate a multi-dimensional display of the type illustrated in FIG. 2, although particles in most of the known-particle volumes 51–56 generally will not be present since many of them represent pathogenic microorganisms. At the same time, the safety of the water can be assessed. One way is to have volunteers drink the water, and be monitored for a few days to see if they become ill. Assuming that the water is safe (and preferably tastes good), the multi-dimensional display of FIG. 2 is entered into the computer memory. Thereafter, the system 10 of FIG. 1 monitors water from the same location (e.g. the same reservoir in the same water treatment plant), as the location where the safe water was taken that produced the background pattern (the multi-dimensional projection). The computer is programmed to generate a multi-dimensional projection in which the eventvectors from the safe water are present, and only the types of particles not present in the safe water background projection, or clusters of a higher density than is present in the multi-dimensional projection, are considered as new clusters. In that event, clusters or groups that approach the status of clusters, that were present in the safe water display, are not considered cluster particles in the multi-dimensional display for the new water that is being monitored. Particles in the new water, whose eventvectors are close to eventvectors in the safe water, may be ignored.

Thus, the invention provides a system and method for monitoring a fluid such as air or water, and especially water, which detects microscopic particles, and which detects the presence of a considerable number of particles of a species that has not been present previously. This is accomplished by analyzing a multi-dimensional projection of the eventvectors, to find clusters where the density of particles lying outside known-particle volumes, is significantly higher than elsewhere. Such cluster indicates invasion of the fluid by a new species, or a sudden increase in a species. This can alert a technician to further examine the fluid. Applicant prefers to generate a background signature representing the eventvectors of particles present when the fluid is safe, as when water was safe to drink. Thereafter, the background signature is considered in analyzing the eventvectors for new water, and deviations from the background signature are looked for, especially clusters.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for identifying unknown-particles that are present in a fluid at a particular location, which includes interrogating particles by directing a beam of light through the fluid and detecting light scattered from the beam in a plurality of different directions to detectors, when a particle passes through a detection zone that lies along said beam, and recording the outputs of said detectors for an event to produce an event vector, which includes establishing data in a memory that represents a multi-dimensional projection wherein groups of eventvectors of each of a plurality of different known-species of particles lie in each of a plurality of separated known-particle volumes of the projection, including:

determining the locations in said memory that represent a multi-dimensional projection, of each of a multiplicity of unknown-particles that do not lie in one of said known-particle volumes;

identifying a possible new species of particles which lies in a location in said multi-dimensional projection, which is outside said known particle volumes, and where the density of particles is at least 50% greater than the average density of particles in said multi-dimensional projection.

2. The method described in claim 1 wherein:

upon identifying a new species of particles in a quantity of fluid, microscopically examining the particles to determine a likely species of the new species of particle.

3. The method described in claim 1 wherein:

said step of identifying a possible new species includes identifying the presence of particles in a volume that is of the same order of magnitude as the average of said known-species volume, and where the density of particles is at least 100% greater than the average density of particles in said multi-dimensional projection.

4. The method described in claim 1 wherein:

in the event that the location of the new species of particles is close to a first one of said known-particle volumes, taking the step of examining particles of said new species to determine if its species is the same as the species of said first known-particle volume, and if so, expanding the volume of said first known-particle volume to include the volume of said new species.

5. The method described in claim 1 including:

recording a safe background pattern of eventvectors for a sample of fluid that has been found to be safe, by at least being free of sufficient amounts of pathogenic microorganisms to cause illness;

said step of identifying a new species includes identifying a cluster of particles whose average density is at least 50% greater than the average density of particles of said safe background pattern.

6. A method for identifying unknown particles that are present in a new sample of fluid at a particular location, which includes interrogating particles by directing a beam of light through the fluid and detecting light scattered from the beam in a plurality of different directions to detectors, when a particle passes though a detection zone that lies along said beam, and recording the outputs of said detectors for an event to produce an event vector, which includes establishing data in a memory that represents a multi-dimensional projection wherein groups of eventvectors of each of a plurality of different known-species of particles lie in each of a plurality of separated known-particle volumes of the projection, including recording a safe background pattern of eventvectors for a safe sample of fluid taken at said particular location, that has been found to be safe;

determining the locations in said memory that represent a multi-dimensional projection, of each of a plurality of unknown particles in said new sample of fluid;

identifying a possible new species of particles which lies at a location in said multi-dimensional projection, which is outside said known-particle volumes, and where the density of particles is at least 50% greater than the average density of particles in the new sample and particles in the safe background pattern.

7. The method described in claim 6 wherein:

said step of identifying a new species includes subtracting the eventvectors of some of the particles in the safe background pattern from the eventvectors of particles in the new pattern, where the particles in the safe background pattern lie at substantially the same locations as particles in the new pattern.

8. Apparatus for identifying unknown-particles that are present in fluid that is to be analyzed, which includes means for generating a light beam and a plurality of detectors that each detects light scattered in a different direction from a detection zone lying along the beam when a particle enters the detection zone and thereby produces an event, the outputs of the detectors for an event constituting an eventvector for the event, the apparatus including a memory that stores a plurality of known-particle patterns for particles that are each of a known-species, where each known-particle pattern comprises multiple eventvectors that each fits into a small known-particle volume of a multi-dimensional projection in which each eventvector is a point in the multi-dimensional projection and the small known-particles volumes that each contains eventvectors of one species are separated from one another, and the apparatus includes a processing circuit that includes a pattern recognition means for indicating whether or not an unknown eventvector produced by an event of an unknown-particle lies in one of the known-particles volumes, wherein:

said processing circuit is constructed to store the eventvectors of those unknown particles that do not lie in one of the known-particle volumes;

said processing circuit includes a clustering algorithm that determines whether or not the eventvectors that do not lie in one of the known-particle volumes, includes one or more groups that forms one or more clusters in said multi-dimensional projection, and which generates an output indicating when a cluster is found.

9. The apparatus described in claim 8 wherein said fluid can contain sufficient amounts of unsafe particles such as pathogenic microorganism and be an unsafe fluid, and said fluid can be free of sufficient amounts of said unsafe particles and therefore be a safe fluid, and wherein:

said memory that stores patterns that each includes multiple eventvectors of known particles that fit into a small known particles volumes, also stores a safe background signature that includes multiple eventvectors representing points in said multi-dimensional projection resulting from the actual generation of eventvectors from at least one sample of fluid that has been tested to be safe, and said processing circuit searches for clusters of those particles not present in the safe background signature.

* * * * *